(12) United States Patent
Wang et al.

(10) Patent No.: US 7,075,087 B2
(45) Date of Patent: Jul. 11, 2006

(54) MULTI-MODALITY DIAGNOSTIC IMAGER

(75) Inventors: Sharon Xiaorong Wang, Hoffman Estates, IL (US); James Frank Caruba, Bartlett, IL (US)

(73) Assignee: Siemens Medical Solutions, USA, Malvern, PA (US)

( * ) Notice: Subject to any disclaimer, the term of this patent is extended or adjusted under 35 U.S.C. 154(b) by 0 days.

(21) Appl. No.: 10/878,883

(22) Filed: Jun. 28, 2004

(65) Prior Publication Data

US 2005/0023471 A1 Feb. 3, 2005

Related U.S. Application Data

(60) Provisional application No. 60/483,567, filed on Jun. 27, 2003.

(51) Int. Cl.
*G01T 1/166* (2006.01)

(52) U.S. Cl. ............................................. 250/363.04

(58) Field of Classification Search ........... 250/363.02, 250/363.04, 363.05, 363.08; 378/19
See application file for complete search history.

(56) References Cited

U.S. PATENT DOCUMENTS

| | | | | |
|---|---|---|---|---|
| 6,147,352 A * | 11/2000 | Ashburn | ................ | 250/363.05 |
| 6,661,865 B1 * | 12/2003 | Popilock | ..................... | 378/19 |
| 6,670,614 B1 * | 12/2003 | Plut et al. | .............. | 250/363.04 |
| 2003/0128801 A1 * | 7/2003 | Eisenberg et al. | ............ | 378/19 |
| 2004/0264628 A1 * | 12/2004 | Besson | ......................... | 378/5 |
| 2005/0006586 A1 * | 1/2005 | Balan et al. | ........... | 250/363.02 |

* cited by examiner

*Primary Examiner*—David Porta
*Assistant Examiner*—Marcus Taningco

(57) ABSTRACT

According to some embodiments, a multimodality diagnostic imaging system having one or more gamma cameras and a flat panel x-ray detector mounted on a common gantry to perform simultaneous FPCT and SPECT studies. In other embodiments, such systems may included EKG devices to gate said studies.

8 Claims, 4 Drawing Sheets

MULTI-MODALITY DIAGNOSTIC IMAGER

CROSS REFERENCE TO A RELATED APPLICATION

This application claims benefit of priority under 35 U.S.C. section 119(e) of U.S. Provisional Application No. 60/483,567 filed Jun. 27, 2003 which is hereby incorporated by reference.

BACKGROUND

1. Field of the Invention

The present invention relates to, inter alia, diagnostic imaging systems, and, in particular to a diagnostic imaging system using multiple modalities. More particularly, some preferred embodiments of the invention relate to methods and apparatuses for the using of digital X-ray and gamma camera modalities in the same diagnostic imaging system.

2. Background Discussion

Medical imaging systems are designed to operate in a number of imaging modalities. Examples of different modalities include simple planar x-ray, Computed Tomography (CT), angiography, simple planar imaging by gamma ray cameras, Single Photon Emission Computed Tomography (SPECT), Position Emission Tomography (PET), and others. The particular characteristics of each modality lend themselves to particular applications.

Diagnostic imaging systems which use multiple imaging modalities have been and continue to be developed. These multimodality systems can yield synergistic advantages above and beyond just the advantages of each specific modality. For example, it is known in the art advantage is gained by combining SPECT and CT in a dual-modality system with each mode mounted on separate gantries with the patient supported and transported between them. Such a system allows for more accurate fusion of structural (anatomical) CT data and functional (disease) SPECT data due to decreased patient movement. Spatial image fusion of conventional CT with SPECT often are inaccurate due to patient motion during the long SPECT data acquisition period. Moreover, the lack of a common gantry increases error in the fusion of the structural (anatomical) and functional images. This problem is exacerbated by the use of traditional-style cylindrical CT detectors, which contributes to vibration and other motion, further degrading image fusion. Cylindrical CT detectors are used to perform spiral CT scans. Furthermore, such cylindrical CT detectors are bulky and expensive.

A further problem is that as the CT data have to be taken either before or after the SPECT data are acquired, the conventional CT combined with SPECT cannot realize image registration in time domain, which limits the usefulness of the system in many motion related clinical studies. For example, in cardiac studies, image registration for image fusion is difficult due to the motion of the heart.

Alternative x-ray detectors using solid state systems are available. Such solid states systems use semiconductors such as amorphous silicon. Other systems have been proposed which use overlapping layers to detect both emissive and transmitted radiation. However such overlapping layer systems have questionable sensitivity and resolution.

There remains a need in the art for a system which takes advantage of the advantages of image fusion using a common gantry and detectors with common geometry, which can promote motion related clinical studies while avoiding the problems of a size and cost problems of a cylindrical CT detector.

SUMMARY OF THE PREFERRED EMBODIMENTS

The preferred embodiments of the present invention can significantly improve upon existing methods and/or apparatuses. According to some embodiments of the invention, a multimodality diagnostic imaging system having one or more gamma cameras and a flat panel x-ray detector mounted on a common gantry to perform CT and SPECT studies. Preferably, such studies are performed with alternative frame acquisition between CT and SPECT. In other embodiments, such systems may include EKG devices to gate said studies.

According to other embodiments of the present invention, a method performing a multimodality scanning includes the steps of providing a gantry having a receiving aperture, providing a flat panel x-ray detector mounted to rotate about the receiving aperture and providing a gamma ray detector mounted to rotate about the receiving aperture. Further steps include acquiring data for a FPCT scan using said x-ray detector, rotating the flat panel x-ray detector about the aperture, acquiring data for a SPECT study with said gamma camera and rotating the gamma camera about the aperture.

The above and/or other embodiments, aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

BRIEF DESCRIPTION OF THE DRAWINGS

The preferred embodiments of the present invention, as well as further objects, features and advantages of the preferred embodiments will be more fully understood with reference to the following detailed description of the preferred embodiments, when taken in conjunction with the accompanying drawings, wherein.

DETAILED DESCRIPTION OF THE PREFERRED EMBODIMENTS

Figure 1:
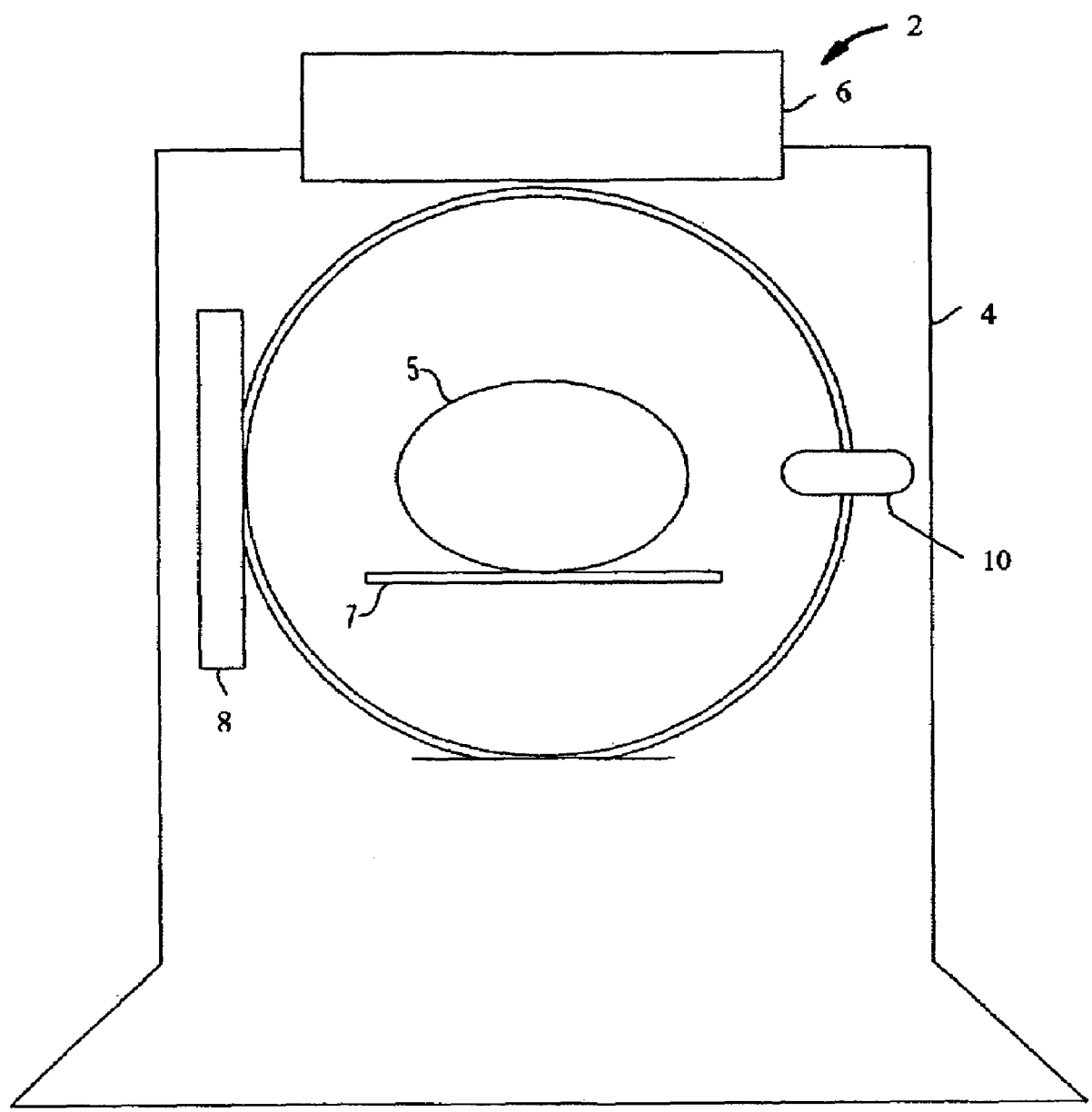
FIG. 1 is a sectional view of a multimodality imaging system including one X-ray detector and one gamma ray detector, which may be employed in some embodiments of the present invention.

FIG. 1 depicts an embodiment of the present invention. Multimodality imaging system 2 has a single head gamma camera configuration. Such a system is composed of a common gantry 4. A patient 5 will be laid on a table 7. A gamma ray detector 6 and a flat panel digital X-ray detector (FPDXD) 8 are mounted to the gantry to rotate around the axis of the gantry. X-ray tube 10 is always opposite the FPDXD 8. In another embodiment, FPDXD 8 and x-ray tube 10 are at a fixed angle from each other. In another embodiment, they may be at a variable angle from each other.

Figure 2:
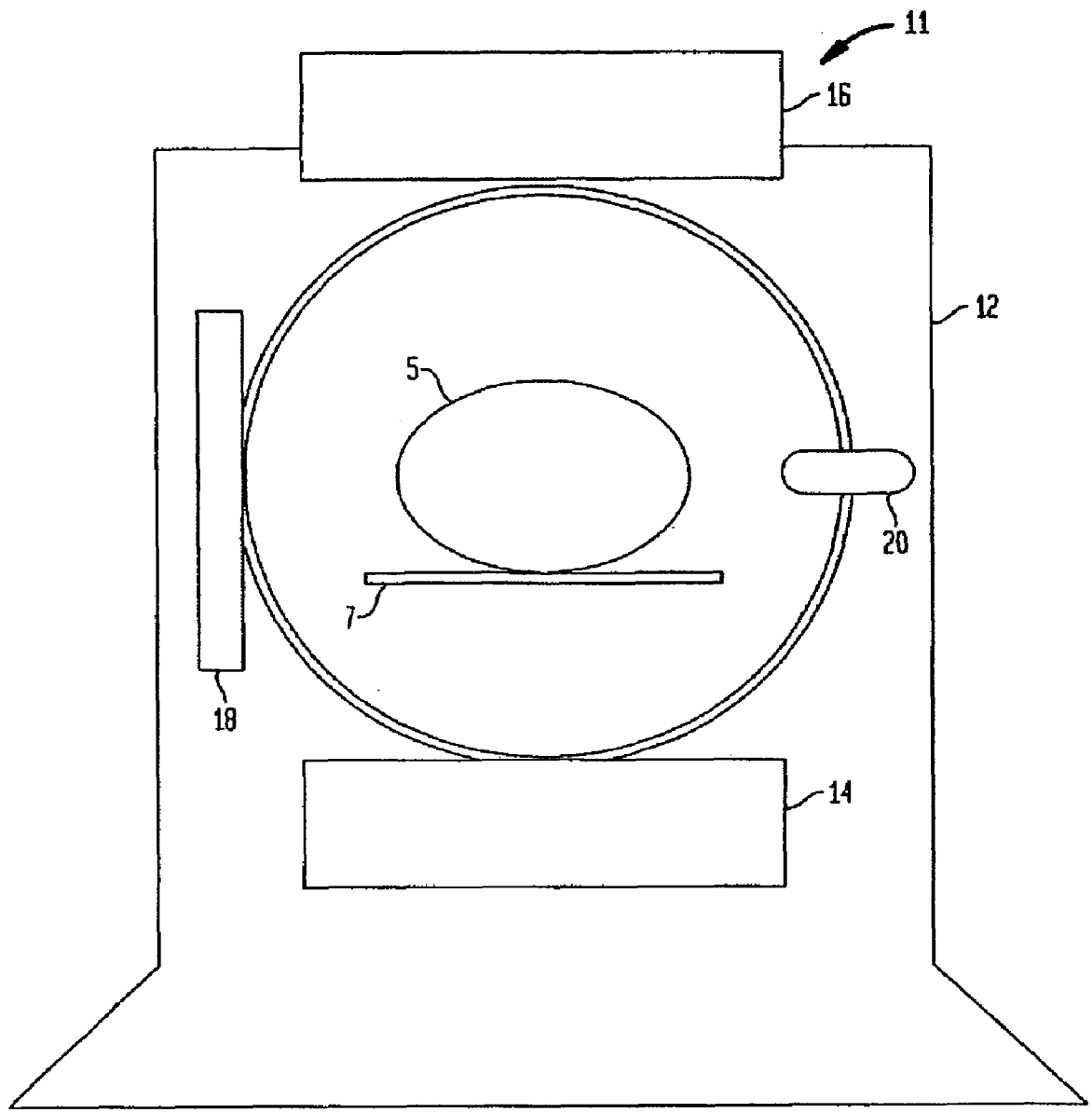
FIG. 2 is a sectional view of a multimodality imaging system including one X-ray detector and two gamma ray detectors in a substantially parallel orientation, which may be employed in some embodiments of the present invention.

FIG. 2 shows another embodiment of the present invention. Multimodality imaging system 11 shows a parallel dual head gamma camera configuration. Such a system is includes a common gantry 12. A first gamma ray detector 14 and a second gamma ray detector 16 are mounted to gantry 12 such that they may rotate about the axis of the gantry. Also on the common gantry 12 is a flat panel digital X-ray detector (FPDXD) 18. X-ray tube 20 is always opposite the FPDXD 18. In one embodiment, FPDXD 18 and gamma camera 10 are at a fixed angle from each other. In another embodiment, they may be at a variable angle from each other.

Figure 3:
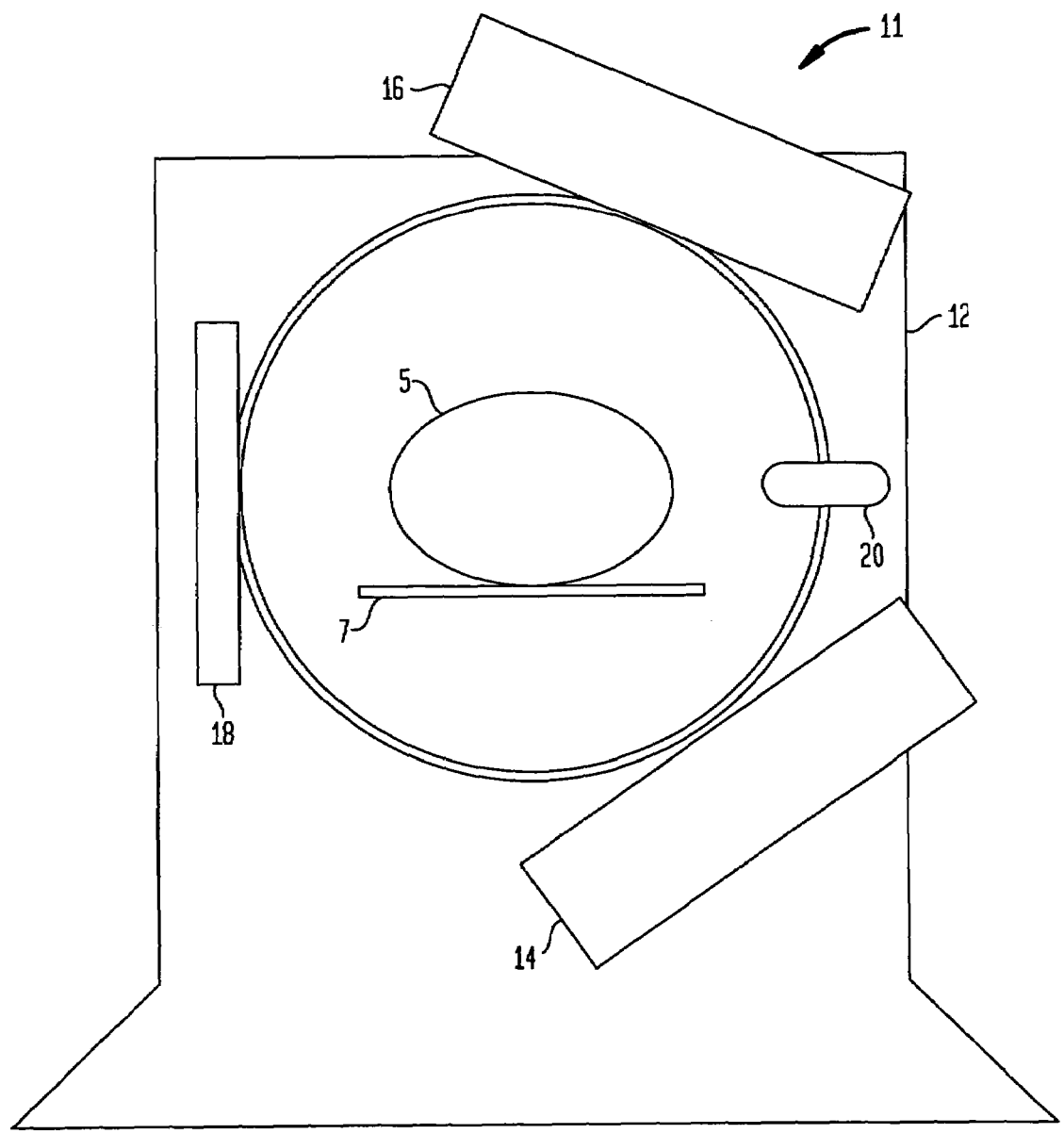
FIG. 3 is a sectional view of a multimodality imaging system including one X-ray detector and two gamma ray detectors at variable angle, which may be employed in some embodiments of the present invention.

FIG. 3 shows yet another embodiment of the present invention similar to FIG. 2. However, multimodality imaging system 22 is shown with gamma cameras 14 and 16 at a variable angle. All other elements are similar to the embodiment of FIG. 2.

The gamma ray detectors, FPDXD and x-ray tubes described are mounted to the gantry around the axis of rotation.

Figure 4:
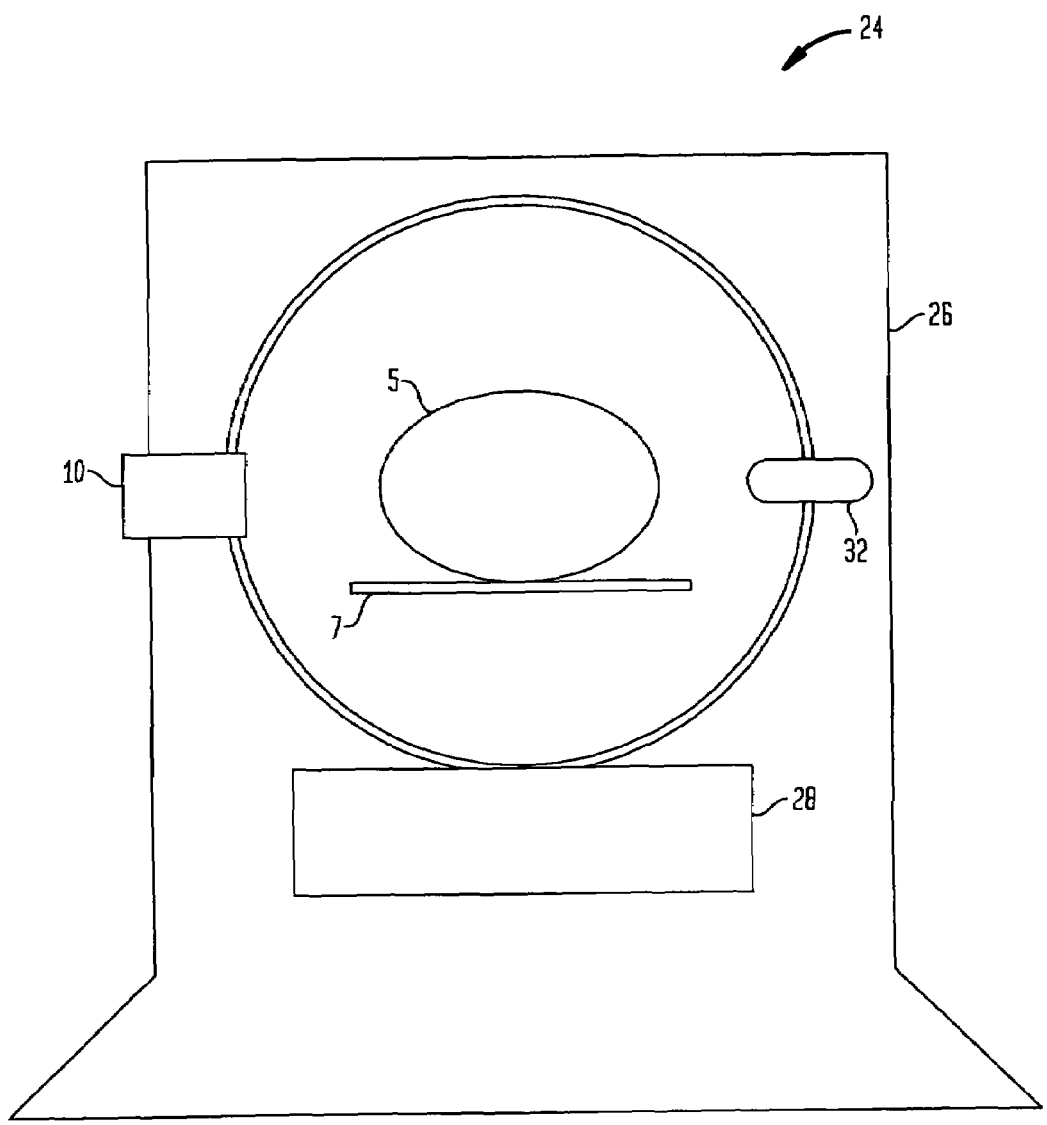
FIG. 4 is sectional view of a multimodality imaging system including a bar X-ray detector-and one gamma ray detector, which may be employed in some embodiments of the present invention.

FIG. 4 shows yet another embodiment of the present invention. The multimodality imaging system 24 is shown with a common gantry 26. A single gamma camera 28 and a single bar X-ray detector 30 are both mounted on the gantry 26. X-ray tube 32 is opposite bar X-ray detector 30.

The multimodality systems shown in the above embodiments are capable of many modes of operation. The FPDXD is capable of performing simple planar X-rays, at a potentially high resolution. If the FPDXD system is rotated about the patient axis, it capable of performing a CT scan, thus making it a Flat Panel Computed Tomography system, or FPCT system. Further, such a system is capable of taking planar gamma camera images. Further, such a system is capable of performing SPECT studies.

In isolation, performing the above functions is well known to those skilled in the art. However, the various embodiments are capable of performing simultaneous SPECT-FPCT studies on a common gantry. Such studies not only yield the advantages of image fusion seen in conventional CT-SPECT studies, but also extend the fusion to the time domain and therefore, realize the CT-SPECT image fusion to the $4^{th}$, or temporal, dimension.

Performing a SPECT scan using gamma cameras involves acquiring data with the gamma camera, advancing the camera by an angle of rotation, acquiring another set of data, repeated, until enough data has been acquired to build a tomographic image. This has been termed a step and shoot technique. In contrast, a spiral CT acquisition of a single slice will take on the order of one second and involve continuous rotation of the CT scanner. This difference in operation makes the registration of tomographic images difficult in the temporal domain. However, an FPCT also operates in a step and shoot method, and its shoot (data acquisition) period is of the same order of magnitude as the gamma camera. Thus, it is possible to interleave data acquisitions by the two modalities. This allows for the potential of registration of tomographic images in the temporal domain.

In addition, the present invention provides multi modalities with the size and cost advantages of using a flat panel x-ray detector. Further, the use of a common gantry reduces movement and vibration, those further increasing the potential quality of image fusion. Preferably, the two scans are done with alternative frame acquisition between CT and SPECT, further reducing patient movement between the two scans. Alternate frame acquisition between CT and SPECT refers to the scan modes at which CT and SPECT data are acquired at an interleaved fashion following a certain pattern.

Yet another embodiment of the present invention uses an EKG signal from the patient being studied to "gate" the SPECT and FPCT studies. This allows data acquisition from both studies to occur only at the same point in the cardiac cycle. Yet another embodiment is the use of FPCT data to detect cardiac motion and thus act as a gate for both FPCT (itself) and SPECT studies.

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

What is claimed is:

1. A multimodality diagnostic imaging system, comprising:
    a gantry having a receiving aperture;
    at least one gamma ray detector mounted for rotation around the receiving aperture;
    an x-ray tube mounted for rotation around the receiving aperture;
    a flat panel x-ray detector mounted for rotation around the receiving aperture;
    wherein said diagnostic imaging system is operable to perform an x-ray computed tomography (CT) scan and a single photon emission computed tomography (SPECT) scan of the same region of a patient placed in said receiving aperture, without requiring movement of said patient with respect to said gantry; and
    an electrocardiogram device, wherein said electrocardiogram device provides a signal to gate the SPECT and CT studies.

2. The system of claim 1, wherein the number of gamma ray detectors is one.

3. The system of claim 1, wherein the number of gamma ray detectors is two.

4. A method of performing multimodality scanning, comprising the steps of:
    performing a single photon emission computed tomography study on a patient using a gantry having a gamma ray detector and a flat panel x-ray detector mounted thereon; and
    performing an x-ray computed tomography study on said patient using said gantry and without requiring any movement of said patient with respect to said gantry;
    wherein said steps of performing a single photon emission computed tomography study and performing an x-ray computed tomography study are gated by a signal from an electrocardiogram device coupled to said patient.

5. A method of registering tomographic images in the temporal domain, comprising the steps of:

(a) acquiring FPCT data of a patient placed in a receiving aperture of a gantry having a flat panel x-ray detector and a gamma ray detector mounted for rotation about said receiving aperture, at a particular angle of rotation of said flat panel x-ray detector;

(b) acquiring SPECT data of said patient at a particular angle of rotation of said gamma ray detector;

(c) incrementing the angle of rotation of said x-ray detector by a predetermined angle;

(d) incrementing the angle of rotation of said gamma ray detector by a predetermined angle;

(e) acquiring FPCT data of said patient at said incremented angle of rotation of said flat panel x-ray detector;

(f) acquiring SPECT data of said patient at said incremented angle of rotation of said gamma ray detector; and (g) triggering the acquisition of said FPCT and SPECT data in response to a signal from an electrocardiogram device coupled to said patient.

6. A method as set forth in claim 5, further comprising the step of repeating steps (c) through (f) for a plurality of angles of rotation about said receiving aperture.

7. A method as set forth in claim 5, wherein rotation of said flat panel x-ray detector and rotation of said gamma ray detector are performed simultaneously.

8. A method as set forth in claim 5, further comprising the step of registering FPCT images with SPECT images acquired at the same angle of rotation with respect to said receiving aperture, to obtain a fused FPCT-SPECT image.

* * * * *